United States Patent
Burton et al.

(10) Patent No.: US 8,382,787 B2
(45) Date of Patent: Feb. 26, 2013

(54) MEDICAL BALLOON WITH ENLARGED TRANSITIONAL RADII

(75) Inventors: David G. Burton, Bloomington, IN (US); Christopher G. Dixon, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1245 days.

(21) Appl. No.: 10/593,376

(22) PCT Filed: Mar. 29, 2005

(86) PCT No.: PCT/US2005/010534
§ 371 (c)(1),
(2), (4) Date: Jul. 9, 2007

(87) PCT Pub. No.: WO2005/097249
PCT Pub. Date: Oct. 20, 2005

(65) Prior Publication Data
US 2007/0282258 A1    Dec. 6, 2007

Related U.S. Application Data

(60) Provisional application No. 60/558,622, filed on Mar. 31, 2004.

(51) Int. Cl.
*A61M 29/02* (2006.01)
(52) U.S. Cl. .................. 606/192; 604/103.07
(58) Field of Classification Search ............. 604/103.06, 604/103.07
See application file for complete search history.

(56) References Cited

U.S. PATENT DOCUMENTS

| | | | |
|---|---|---|---|
| 4,637,396 A | 1/1987 | Cook | 128/344 |
| 4,800,882 A | 1/1989 | Gianturco | 128/343 |
| 4,848,344 A | 7/1989 | Sos et al. | 128/344 |
| 5,324,257 A | 6/1994 | Osborne et al. | 604/53 |
| 5,797,878 A * | 8/1998 | Bleam | 604/196 |
| 5,814,061 A | 9/1998 | Osborne et al. | 606/194 |
| 6,251,094 B1 | 6/2001 | Bleam | 604/96.01 |
| 2003/0139762 A1 * | 7/2003 | Lee | 606/194 |
| 2003/0225434 A1 | 12/2003 | Glantz et al. | 606/194 |

FOREIGN PATENT DOCUMENTS

WO   WO 2005/097249 A1   10/2005

OTHER PUBLICATIONS

International Search Report and Written Opinion from PCT Application No. PCT/US2005/010534 dated Jun. 24, 2005, 6 pages.
U.S. Appl. No. 06/558,622, filed Mar. 2004, Burton et al.

* cited by examiner

*Primary Examiner* — Kathleen Sonnett
*Assistant Examiner* — Sarah W Aleman
(74) *Attorney, Agent, or Firm* — Brinks Hofer Gilson & Lione

(57) ABSTRACT

The present invention provides a medical balloon having enlarged radii, which may be disposed on a dilation catheter. The enlarged radii balloon may reduce the trauma experienced by a patient both during the procedure and when the catheter is removed from the patient. The enlarged radii may provide the deflated balloon with smoother transitions and less mechanical rigidity at the balloon transitions.

11 Claims, 4 Drawing Sheets

MEDICAL BALLOON WITH ENLARGED TRANSITIONAL RADII

BACKGROUND

Medical balloons may be combined with a wide variety of devices and used in a vast array of medical procedures. For example, medical balloons may be combined with a catheter to provide dilation catheters, drainage catheters, and the like.

Dilation catheters rely upon a medical balloon for applying pressure against the interior of a biological conduit, such as a blood vessel, a portion of the urinary tract, and/or a portion of the gastro-intestinal tract. Dilation catheters are useful in a variety of techniques, including gynecological procedures, cardiac procedures, general interventional radiology procedures, and the like.

One example of a cardiac procedure is percutaneous transluminal coronary angioplasty (PTCA). Using this technique, a physician can dilate a narrowed artery by inserting and advancing a catheter with a deflated medical balloon at its tip into the narrowed part of the artery. The plaque is compressed upon inflation of the medical balloon, which dilates the inner diameter of the blood vessel, allowing blood to flow more easily. Following this procedure, the medical balloon is deflated and the catheter removed from the patient's body.

Another procedure employing dilation catheters is stent delivery. A stent may be a wire mesh or a solid tube used to support an artery that has recently been cleared using angioplasty. After being collapsed to a small diameter, the stent may be placed over the medical balloon of the dilation catheter and advanced to the area of the blockage. When the medical balloon is inflated, the stent expands, locks in place, and forms a scaffold, holding the artery open.

One specific use of dilation catheters is in the treatment of obstructed blood vessels. This type of procedure normally begins with insertion of a delivery sheath using the Seldinger or other technique. Delivery sheaths are generally small-diameter plastic tubes and are another type of conduit, through which a catheter may be inserted. Generally, the delivery sheath is inserted through a patient's skin and then into a major blood vessel, for example. The delivery sheath is arranged such that the proximal portion remains on the exterior of the patient, while the distal portion is located in the major blood vessel of interest. Next, the distal portion of a wire guide may be inserted into the exterior and proximal end of the delivery sheath. Then, the wire guide may be passed through the delivery sheath, out the distal end of the delivery sheath, and into the patient. In this fashion, a delivery sheath may be used as a means for the placement of intravascular medical devices into venous or arterial systems following insertion of the delivery sheath through the skin. The delivery sheath may also protect the point of entry into the patient's body from mechanical damage and trauma.

Once inside the patient, the distal end of the wire guide may be advanced into the diseased coronary artery until it reaches the obstruction. After crossing the lesion, or other region to be dilated, the wire guide may be secured such that it remains in this location. During this entire procedure, the proximal end of the wire guide remains at the exterior of the patient.

Next, the distal tip of a dilation catheter may be slid over the proximal end of the previously placed wire guide. The dilation catheter, following the previously placed wire guide, may be advanced into the proximal end of the delivery sheath, through the body of the sheath, out the distal end of the sheath, and then into the patient. The dilation catheter may be advanced over the wire guide until the medical balloon, located toward the distal end of the dilation catheter, is properly positioned adjacent to the lesion. Finally, fluid may be used to inflate the medical balloon to a predetermined size, thus compressing the lesion.

Generally, the medical balloon of a dilation catheter occupies a folded configuration prior to inflation. This configuration may reduce the force necessary to advance the dilation catheter through the conduit, which in turn may reduce the physical trauma to the patient. When the medical balloon on the dilation catheter is inflated, to compress a lesion for example, the medical balloon unfolds. Once unfolded, the medical balloon is generally not capable of again obtaining the folded configuration.

FIG. 1 depicts a longitudinal cross-sectional view of a conventional dilation catheter 100 that includes an elongate catheter body 105, having a proximal end 107 and a distal end 108. The distal end may terminate in a distal tip 110. The conventional dilation catheter body 105 is equipped with a conventional medical balloon 115 (depicted in its unfolded configuration), having a distal balloon end 117 and a proximal balloon end 118. The medical balloon 115 has a distal conical region 120, a proximal conical region 125, and a working length 130, where the working length 130 is defined by the distal conical region 120 and the proximal conical region 125. The medical balloon 115, including the working length 130, the distal conical region 120, and the proximal conical region 125, is formed by a balloon wall 135, enclosing a balloon cavity 140. The balloon wall 135 may form a distal balloon lip 142 and a proximal balloon lip 143. The conventional medical balloon 115 may be attached to the elongate catheter body 105 via the distal balloon lip 142 and the proximal balloon lip 143. For clarity of discussion, the lips 142, 143 are not considered part of the balloon because they do not enclose the balloon cavity 140.

The distal conical region 120 and the proximal conical region 125 each include two taper transitions. There is a distal working length-to-taper transition 145, a distal taper-to-neck transition 150, a proximal working length-to-taper transition 155, and a proximal taper-to-neck transition 160. The distal working length-to-taper transition 145 is located between the working length 130 and the distal conical region 120. The proximal working length-to-taper transition 155 is located between the working length 130 and the proximal conical region 125. The distal taper-to-neck transition 150 is located between the distal conical region 120 and the elongate catheter body 105. The proximal taper-to-neck transition 160 is located between the proximal conical region 125 and the elongate catheter body 105.

The conventional medical balloon 115, in its unfolded configuration, includes sharp bends at the balloon working length-to-taper transitions, 145 and 155, and at the taper-to-neck transitions, 150 and 160. The sharp bends at the transitions of the conventional medical balloon 115 do not easily collapse after the balloon has been inflated and can make it difficult to pull the balloon back through the conduit after use. The harder it is to remove the collapsed balloon after use, the more patient trauma may occur at the entry site during removal of the device. Furthermore, if the conventional medical balloon 115 freezes in the delivery sheath and the physician exerts excess force on the conventional dilation catheter 100 in attempt to remove it from the sheath, mechanical failure of the device may occur. A situation that may necessitate making a much larger incision in the patient to remove the device. A medical balloon that facilitates removal of dilation catheters from conduits may beneficially reduce patient trauma.

BRIEF SUMMARY

An inflatable medical balloon is provided having enlarged transitional radii. These medical balloons can provide many benefits, including a reduction in during and post-procedure trauma to the patient. The enlarged transitional radii may provide smoother transitions and/or less mechanical rigidity at the balloon transitions, which may decrease the force required to pull the deflated balloon back through a conduit after use.

In another aspect, the enlarged transitional radii may provide a medical balloon that more easily conforms to the shape of a conduit, thus allowing easier travel through the conduit.

The reduction in removal force may directly reduce trauma at the entry point to the patient. The reduction in removal force also may reduce mechanical damage to the distal portion of the delivery sheath, thus further reducing trauma to the patient when the delivery sheath is removed from the entry point. In another aspect, the trauma to a biological conduit also may be reduced.

In one aspect, a dilation catheter is provided that includes at least one lumen in fluid communication with a medical balloon having enlarged transitional radii at at least one of a proximal taper-to-neck transition, a proximal working length-to-taper transition, a distal taper-to-neck transition, and a distal working length-to-taper transition.

In another aspect, a medical balloon is provided having enlarged transitional radii at at least one of a proximal taper-to-neck transition, a proximal working length-to-taper transition, a distal taper-to-neck transition, and a distal working length-to-taper transition.

In another aspect, a method of making a dilation catheter is provided that includes fixing to an elongate catheter body a medical balloon having enlarged transitional radii at least one of a proximal taper-to-neck transition, a proximal working length-to-taper transition, a distal taper-to-neck transition, and a distal working length-to-taper transition.

In another aspect, the force required to remove a dilation catheter from a conduit is reduced by inserting the dilation catheter through the conduit so a medical balloon having enlarged transitional radii fixed on the catheter emerges from the conduit, inflating the balloon, deflating the balloon, and exerting a force against the catheter to remove the balloon from the conduit, where the removal force is reduced in relation to a conventional dilation catheter having a medical balloon lacking enlarged transitional radii.

Other methods, features, and advantages of the invention will be, or will become, apparent to one with skill in the art upon examination of the following figures and detailed description. It is intended that all such additional systems, methods, features, and advantages are included within this description, are within the scope of the invention, and are protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention.

DETAILED DESCRIPTION

Figure 2:
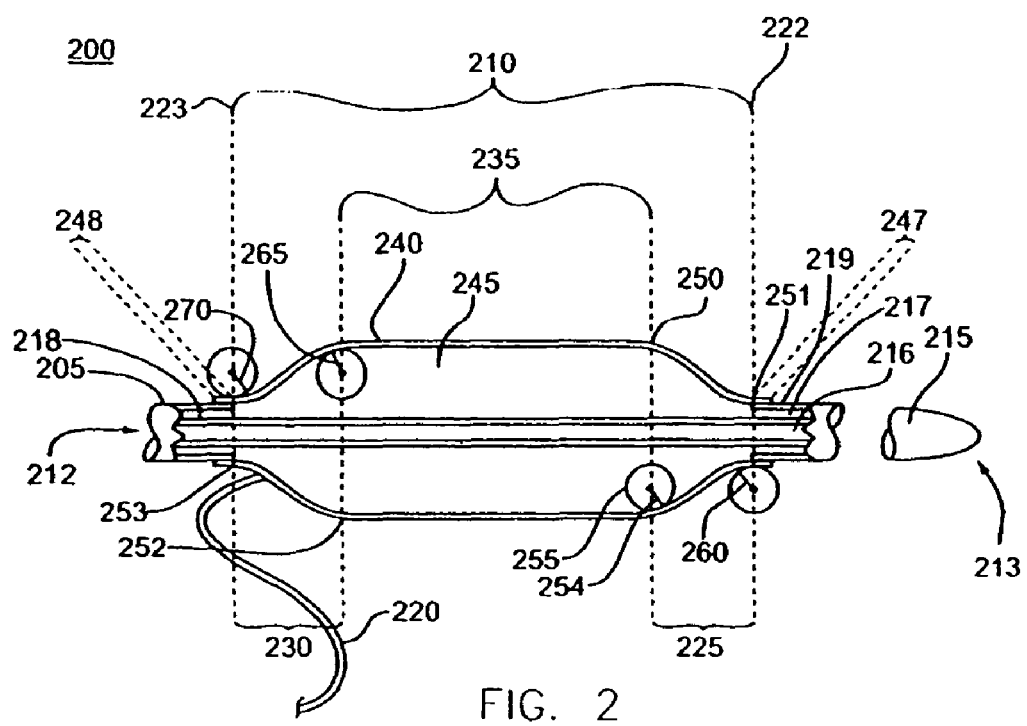
FIG. 2 depicts a longitudinal cross-sectional view of a dilation catheter in accordance with the present invention that is equipped with an enlarged transitional radii medical balloon in an unfolded configuration.

FIG. 2 depicts a longitudinal cross-sectional view of a dilation catheter 200 having an elongate catheter body 205 and a deflated medical balloon 210 embodying aspects of the present invention. The catheter body 205 may have a longitudinal axis extending between a proximal end 212 and a distal end 213. The distal end 213 may terminate in a distal tip 215. The catheter body 205 may include one or more lumens, such as an inner lumen 216 and an outer lumen 217, defined by a plurality of tubes, such as inner tube 218 and outer tube 219. In one aspect, the inner tube 218, and its corresponding inner lumen 216, may not be present, leaving only outer lumen 217. In another aspect, one or more of the lumens, such as the inner lumen 216 or the outer lumen 217, may be in fluid communication with a balloon cavity 245. Furthermore, the exterior lumen 220 may be in fluid communication with the balloon cavity 245. The dilation catheter 200 also may possess an exterior lumen 220, which may be located to the exterior of the elongate catheter body 205 on which the medical balloon 210 is mounted.

The deflated medical balloon 210 may have a distal balloon end 222 and a proximal balloon end 223. The medical balloon 210 may have a distal conical region 225, a proximal conical region 230, and a working length 235 defined by the distal and proximal conical regions 222 and 223, respectively. The distal conical region 225 and the proximal conical region 230 may be described as transitions between the elongate catheter body 205 and the working length 235. The medical balloon 210, including the working length 235, the distal conical region 225, and the proximal conical region 230, may be formed by a balloon wall 240, enclosing the balloon cavity 245. The balloon wall 240 may form a distal balloon lip 247 and a proximal balloon lip 248. The medical balloon 210 may be attached to the elongate catheter body 205 via the distal balloon lip 247 and the proximal balloon lip 248. For clarity of discussion, the lips 247, 248 are not considered part of the balloon because they do not enclose the balloon cavity 245.

The distal conical region 225 and the proximal conical region 230 each include two taper transitions. There is a distal working length-to-taper transition 250, a distal taper-to-neck transition 251, a proximal working length-to-taper transition 252, and a proximal taper-to-neck transition 253. The distal working length-to-taper transition 250 is located between the working length 235 and the distal conical region 225. The proximal working length-to-taper transition 252 is located between the working length 235 and the proximal conical region 230. The distal taper-to-neck transition 251 is located between the distal conical region 225 and the elongate catheter body 205. The proximal taper-to-neck transition 253 is located between the proximal conical region 230 and the elongate catheter body 205.

The curvature of the working length-to-taper transitions, 250 and 252, and the taper-to-neck transitions, 251 and 253, may be expressed in terms of an enlarged radius, corresponding to a circle 255 scribed in each transition. For example, a distal working length-to-taper transition 250 has an enlarged distal working length-to-taper radius 254. In this manner, the length of the enlarged radius of the scribed circle 255 provides a way to measure the curvature or rate at which one portion of the balloon transitions into another portion of the balloon or into the catheter body 205. In addition to the enlarged distal working length-to-taper radius 254, there is also an enlarged distal taper-to-neck radius 260, an enlarged proximal working length-to-taper radius 265, and an enlarged proximal taper-to-neck radius 270. The lengths of the enlarged radii 254, 260, 265, and 270 correspond to the values that may be measured when the medical balloon 210 is unfolded.

Figure 1:
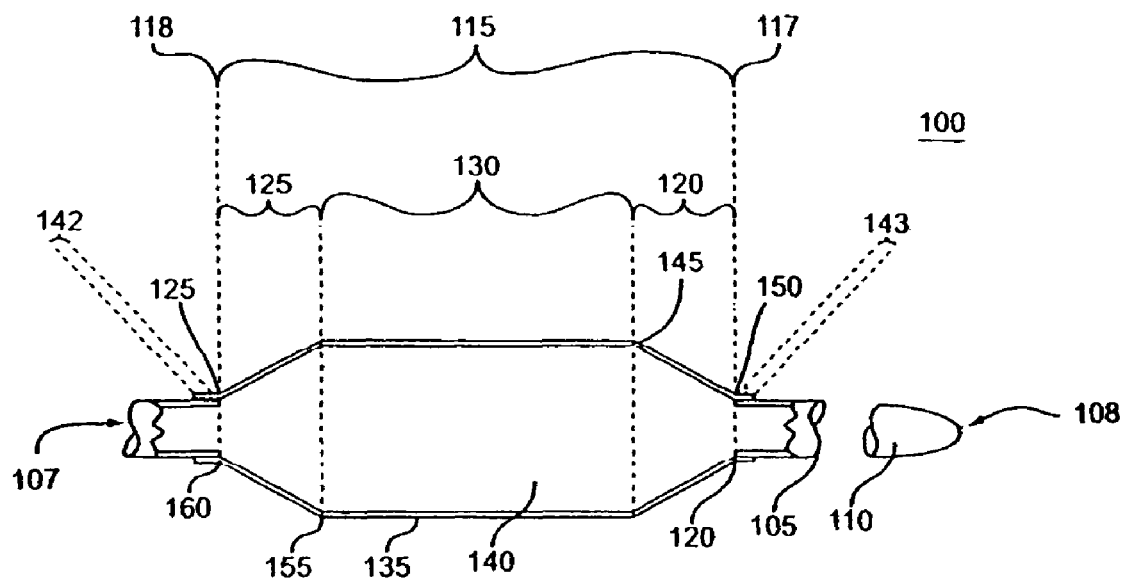
FIG. 1 depicts a longitudinal cross-sectional view of a conventional dilation catheter in an unfolded configuration.

Because each radius has a length that may be measured in millimeters (mm), variances in transition rates may be determined by comparing the lengths of the radii. For example, to express a slower, gentler curvature from one portion of the balloon to another requires a larger circle, having a larger radius, than would be required to express a rapid curve. Similarly, a balloon having sharp bends connecting one portion of the balloon to another, such as the conventional medical balloon 115 depicted in FIG. 1, would have no radius or a very small radius.

Unlike conventional medical balloon designs, the balloon transitions 250, 251, 252, and 253 may have curvature represented as the enlarged radii 254, 260, 265, and 270, respectively. For a medical balloon having an 8 mm diameter and a 4 cm length, the enlarged radii may be at least 1.9 mm or may each independently range from about 1.9 mm to about 13 mm. In one aspect, the enlarged radii 254, 260, 265, and 270 also may be at least 4 mm or may each independently range from about 4 mm to about 12 mm. In another aspect, the enlarged radii 254, 260, 265, and 270 also may be at least 7 mm or may each independently range from about 7 mm to about 12 mm.

In one aspect, at least one transition of the proximal taper-to-neck transition 253, the proximal working length-to-taper transition 252, the distal taper-to-neck transition 251, and the distal working length-to-taper transition 250 comprises a radius from about 1.9 mm to about 13 mm. In one aspect, at least one transition of the proximal taper-to-neck transition 253, the proximal working length-to-taper transition 252, the distal taper-to-neck transition 251, and the distal working length-to-taper transition 250 comprises a radius from about 4 mm to about 13 mm. In one aspect, at least one transition of the proximal taper-to-neck transition 253, the proximal working length-to-taper transition 252, the distal taper-to-neck transition 251, and the distal working length-to-taper transition 250 comprises a radius from about 7 mm to about 13 mm. In one aspect, at least one transition of the proximal taper-to-neck transition 253, the proximal working length-to-taper transition 252, the distal taper-to-neck transition 251, and the distal working length-to-taper transition 250 comprises a radius of at least 1.9 mm. In one aspect, at least one transition of the proximal taper-to-neck transition 253, the proximal working length-to-taper transition 252, the distal taper-to-neck transition 251, and the distal working length-to-taper transition 250 comprises a radius of at least 4 mm. In one aspect, at least one transition of the proximal taper-to-neck transition 253, the proximal working length-to-taper transition 252, the distal taper-to-neck transition 251, and the distal working length-to-taper transition 250 comprises a radius of at least 7 mm.

In one aspect, the radii 265 and 270 may be substantially the same. In another aspect, the radii 254 and 260 may be substantially the same. Furthermore, the radii 254, 260, 265, and 270 may be substantially the same. In another aspect, the radii 265 and 270 may be substantially the same as each other, but different from 254 and 260, which may be substantially the same as each other. In another aspect, 254, 260, 265, and 270 may all be different.

As shown in Table 1 below, the enlarged radii 254, 260, 265, and 270 of the medical balloon 210 may provide for a substantial reduction in the force required to pull the deflated balloon through a delivery sheath.

TABLE 1

| Entry | Balloon Radii (mm) | Average force required to withdraw balloon through sheath (N) |
| --- | --- | --- |
| 1 | 0.1 | 2.2 |
| 2 | 3.2 | 2.0 |
| 3 | 6.4 | 2.1 |
| 4 | 8.9 | 1.5 |
| 5 | 11.4 | 1.2 |

Table 1 compares the force required to remove a deflated conventional medical balloon from a delivery sheath (Entry 1) to the force required to remove a deflated medical balloon embodying aspects of the present invention from a delivery sheath (Entries 2-5). The data in Table 1 were collected using a series of balloons in which the radii were varied, but the balloon diameter and length were held constant. In each case, the balloon diameter was 8 mm and the balloon length was 4 cm.

Entry 1 represents a conventional medical balloon with radii of 0.1 mm. The conventional medical balloon of Entry 1 had a removal force of 2.2 N. Entries 2 through 5 represent medical balloons having enlarged radii ranging from 3.2 mm to 11.4 mm, in accordance with the present invention.

Table 1 demonstrates that medical balloons having the enlarged radii of the present invention may require less force to withdraw through a delivery sheath. For example, Entry 5 provides a 43% reduction in the amount of force required to remove the deflated enlarged radii medical balloon from the sheath when compared to the deflated conventional medical balloon. In addition to reducing the removal force, the smoothed transitions provided by the enlarged radii may increase the comfort level of the patient during the procedure and lessen the trauma to the biological conduits as the catheter is guided through the patient.

A decrease in the force required to remove the medical balloon from the delivery sheath also may protect the mechanical integrity of the catheter because if the physician doesn't have to pull as hard to remove the medical balloon, then there may be less strain on the catheter. This can reduce the chance of the medical balloon detaching in the body cavity and requiring a large incision for removal. Furthermore, if the medical balloon can be more easily removed from the delivery sheath, the risk of damaging the distal portion of the delivery sheath may be reduced. This may be beneficial, since removal of a damaged delivery sheath also may result in additional trauma to the patient, especially if the removal of the medical balloon causes a flaring in the distal end of the sheath. Finally, a reduction in the force required to remove the medical balloon may allow the physician to more easily determine if problems are occurring during the removal of the catheter. For example, the physician may be able to more readily evaluate when the dilation catheter has become ensnared by something within the delivery sheath or within a biological conduit.

The radius of enlarged radii can vary depending on the diameter of the medical balloon. Table 2 below provides a series of medical balloons and corresponding preferred enlarged radii, which may exhibit a reduction in removal force when compared to conventional medical balloons of the same diameter. As may be seen from the Table, smaller diameter medical balloons have smaller preferred enlarged radii lengths due to their smaller size. The enlarged radii medical balloons of Table 2 also may demonstrate a beneficial reduction in removal force as was previously observed for the 4×8 medical balloon in Table 1.

TABLE 2

| Approximate Balloon Diameter (mm) | Preferred Enlarged Radii Range (mm) | More Preferred Enlarged Radii Range (mm) | Presently Preferred Enlarged Radii (mm) |
|---|---|---|---|
| 3 | 0.97-3.3 | 1.3-3.3 | 2.5 |
| 4 | 1.8-4.7 | 2.5-4.7 | 3.2 |
| 5 | 2.4-6.4 | 3.2-6.4 | 4.7 |
| 6 | 3.5-8.3 | 4.7-8.3 | 6.4 |
| 7 | 4.8-10.2 | 6.4-10.2 | 8.3 |
| 8 | 6.2-11.4 | 8.3-11.4 | 8.9 |
| 9 | 6.7-13.3 | 8.9-13.3 | 10.8 |
| 10 | 8.1-15.2 | 10.8-15.2 | 12.1 |
| 11 | 9.1-17.1 | 12.1-17.1 | 13.3 |
| 12 | 9.9-19.1 | 13.3-19.1 | 14.9 |
| 14 | 11.2-22.9 | 14.9-22.9 | 17.8 |
| 15 | 13.3-25.4 | 17.8-25.4 | 19.1 |

Figure 3:
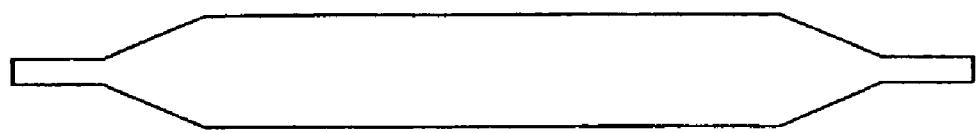
FIG. 3 depicts a conventional medical balloon having conventional radii of 0.127 mm.
Figure 4:
FIG. 4 depicts a medical balloon embodying elements of the present invention having enlarged radii of about 1.9 mm.
Figure 5:
FIG. 5 depicts a medical balloon embodying elements of the present invention having enlarged radii of about 3.2 mm.
Figure 6:
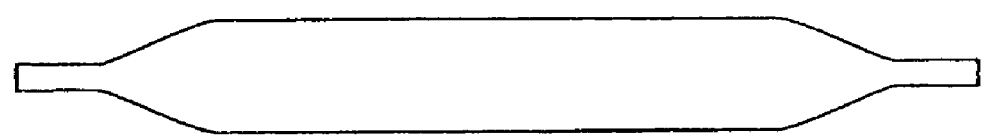
FIG. 6 depicts a medical balloon embodying elements of the present invention having enlarged radii of about 5.1 mm.
Figure 7:
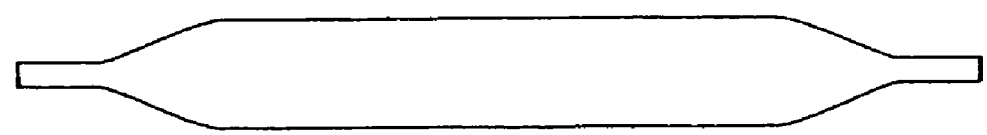
FIG. 7 depicts a medical balloon embodying elements of the present invention having enlarged radii of about 6.4 mm.
Figure 8:
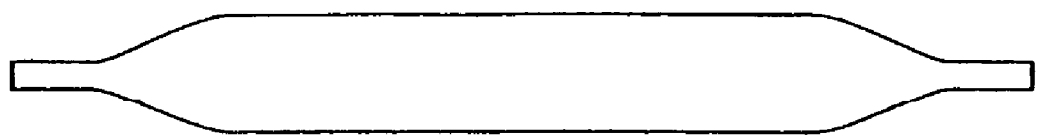
FIG. 8 depicts a medical balloon embodying elements of the present invention having enlarged radii of about 7.6 mm.
Figure 9:
FIG. 9 depicts a medical balloon embodying elements of the present invention having enlarged radii of about 8.9 mm.
Figure 10:
FIG. 10 depicts a medical balloon embodying elements of the present invention having enlarged radii of about 10.2 mm.
Figure 11:
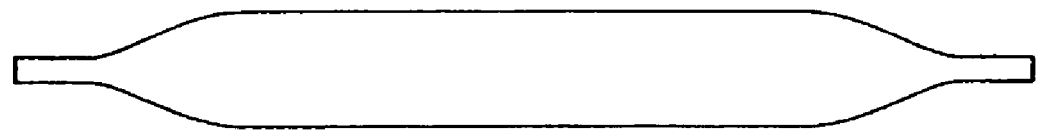
FIG. 11 depicts a medical balloon embodying elements of the present invention having enlarged radii about 11.4 mm.
Figure 12:
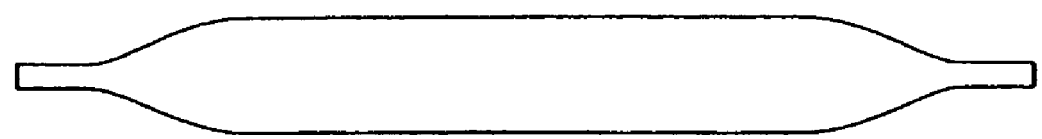
FIG. 12 depicts a medical balloon embodying elements of the present invention having enlarged radii of about 12.7 mm.

FIG. 3 depicts a deflated conventional medical balloon having radii of 0.127 mm. FIGS. 4-12 depict deflated medical balloons having enlarged radii ranging from about 1.9 mm (FIG. 4) to about 12.7 mm (FIG. 13). While the enlarged radii are initially difficult to perceive visually, by the time a radius of about 5.1 mm is reached (FIG. 6), the smoothing of the transitions is readily apparent. Even though difficult to visually perceive, the enlarged radii of FIGS. 4 and 5 can have a marked effect on the ability of the medical balloon to conform to and be removed from various conduits.

Figure 13A:
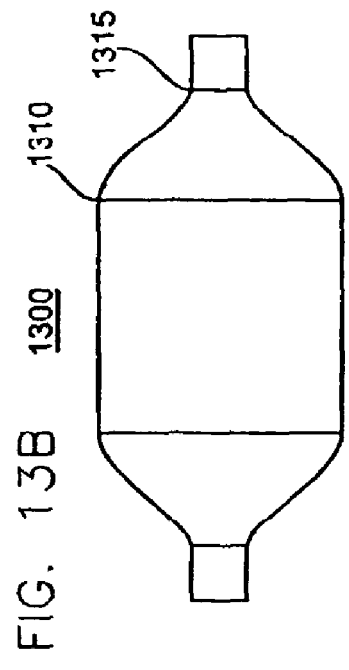
FIGS. 13A-D depict a comparison between an unfolded conventional medical balloon and an unfolded medical balloon embodying elements of the present invention before and after inflation.
Figure 13B:
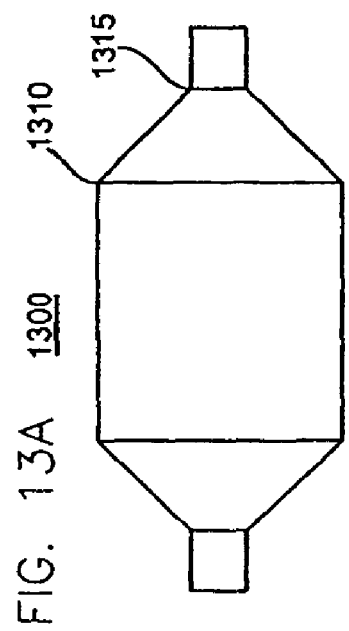
Figure 13C:
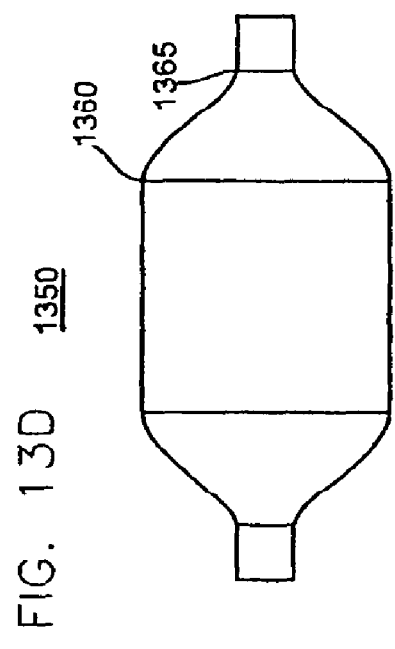
Figure 13D:
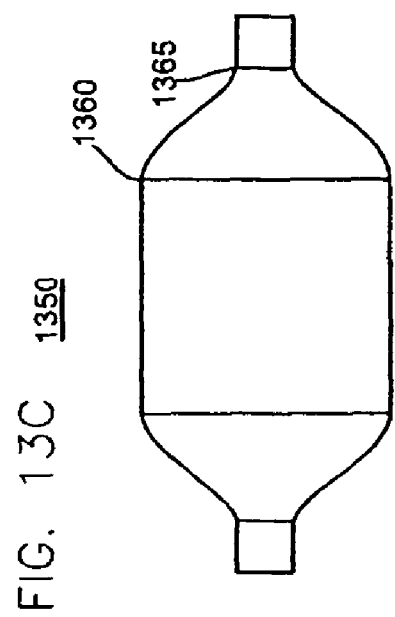

FIGS. 13A-D depict a comparison between a conventional medical balloon 1300 and a medical balloon having enlarged radii 1350 before and after inflation. After unfolding, it is apparent that the conventional medical balloon 1300 has sharp bends at its transitions 1310 and 1315 (FIG. 13A). In direct contrast, FIG. 13C depicts an unfolded medical balloon having smoothed transitions 1360 and 1365 resulting from enlarged radii. When the conventional medical balloon 1300 is inflated, as depicted in FIG. 13B, the inflation pressure smoothes the sharp bends 1310 and 1315. Similarly, when the enlarged radii medical balloon 1350 is inflated, as shown in FIG. 13D, it takes on a similar appearance to the inflated conventional medical balloon 1300 having pressure distended sharp bends. Even though the conventional medical balloon 1300 may resemble a medical balloon having enlarged radii when inflated, when deflated, the differences in the transitions are readily apparent.

It is intended that the foregoing detailed description be regarded as illustrative rather than limiting, and that it be understood that it is the following claims, including all equivalents, that are intended to define the spirit and scope of this invention.

What is claimed is:

1. A dilation catheter comprising:
an elongate catheter body with at least one lumen; and
a medical balloon disposed about a portion of the elongate catheter body in fluid communication with the lumen, the medical balloon comprising:
a proximal region and a distal region;
a balloon working length intermediate the proximal region and the distal region;
a proximal working length-to-taper transition;
wherein the proximal working length-to-taper transition comprises a radius before inflation from:
0.97 to 3.3 mm when the balloon has a working length diameter of about 0.3 mm,
1.8 to 4.7 mm when the balloon has a working length diameter of about 4 mm,
2.4 to 6.4 mm when the balloon has a working length diameter of about 5 mm,
3.5 to 8.3 mm when the balloon has a working length diameter of about 6 mm,
4.8 to 10.2 mm when the balloon has a working length diameter of about 7 mm,
6.2 to 11.4 mm when the balloon has a working length diameter of about 8 mm,
6.7 to 13.3 mm when the balloon has a working length diameter of about 9 mm,
8.1 to 15.2 mm when the balloon has a working length diameter of about 10 mm,
9.1 to 17.1 mm when the balloon has a working length diameter of about 11 mm,
9.9 to 19.1 mm when the balloon has a working length diameter of about 12 mm,
11.2 to 22.9 mm when the balloon has a working length diameter of about 14 mm, or
13.3 to 25.4 mm when the balloon has a working length diameter of about 15 mm.

2. The dilation catheter of claim 1, where the radius is from:
1.3 to 3.3 mm when the balloon has a working length diameter of about 3 mm,
2.5 to 4.7 mm when the balloon has a working length diameter of about 4 mm,
3.2 to 6.4 mm when the balloon has a working length diameter of about 5 mm,
4.7 to 8.3 mm when the balloon has a working length diameter of about 6 mm,
6.4 to 10.2 mm when the balloon has a working length diameter of about 7 mm,
8.3 to 11.4 mm when the balloon has a working length diameter of about 8 mm,
8.9 to 13.3 mm when the balloon has a working length diameter of about 9 mm,
10.8 to 15.2 mm when the balloon has a working length diameter of about 10 mm,
12.1 to 17.1 mm when the balloon has a working length diameter of about 11 mm,
13.3 to 19.1 mm when the balloon has a working length diameter of about 12 mm,
14.9 to 22.9 mm when the balloon has a working length diameter of about 14 mm, or
17.8 to 25.4 mm when the balloon has a working length diameter of about 15 mm.

3. The dilation catheter of claim 1, where the radius is:
about 2.5 mm when the balloon has a working length diameter of about 3 mm, about 3.2 mm when the balloon has a working length diameter of about 4 mm,
about 4.7 mm when the balloon has a working length diameter of about 5 mm,
about 6.4 mm when the balloon has a working length diameter of about 6 mm,
about 8.3 mm when the balloon has a working length diameter of about 7 mm,
about 8.9 mm when the balloon has a working length diameter of about 8 mm,
about 10.8 mm when the balloon has a working length diameter of about 9 mm,
about 12.1 mm when the balloon has a working length diameter of about 10 mm,
about 13.3 mm when the balloon has a working length diameter of about 11 mm,
about 14.9 mm when the balloon has a working length diameter of about 12 mm,
about 17.8 mm when the balloon has a working length diameter of about 14 mm, or
about 19.1 mm when the balloon has a working length diameter of about 15 mm.

4. The dilation catheter of claim 1, where the proximal working length-to-taper radius is substantially equal to a distal working length-to-taper radius.

5. The dilation catheter of claim 1, where a proximal taper-to-neck radius, the proximal working length-to-taper radius, a distal taper-to-neck radius, and a distal working length-to-taper radius are substantially equal.

6. The dilation catheter of claim 1, where a proximal taper-to-neck radius and a distal taper-to-neck radius are substantially equal to each other.

7. The dilation catheter of claim 6, where the proximal working length-to-taper radius and a distal working length-to-taper radius are different from the proximal taper-to-neck radius and the distal taper-to-neck radius.

8. The dilation catheter of claim 1, where the proximal working length-to-taper radius and a distal working length-to-taper radius are different.

9. A method of reducing the force required to remove a dilation catheter from a conduit, comprising:
 (a) inserting the dilation catheter through the conduit, so a medical balloon disposed on the catheter emerges from the conduit, wherein the dilation catheter includes an elongate catheter body, the medical balloon comprising:
 a proximal region and a distal region;
 a balloon working length intermediate the proximal region and the distal region;
 a proximal working length-to-taper transition;
 wherein the proximal working length-to-taper transition comprises a radius before inflation from:
 0.97 to 3.3 mm when the balloon has a working length diameter of about 3 mm,
 1.8 to 4.7 mm when the balloon has a working length diameter of about 4 mm,
 2.4 to 6.4 mm when the balloon has a working length diameter of about 5 mm,
 3.5 to 8.3 mm when the balloon has a working length diameter of about 6 mm,
 4.8 to 10.2 mm when the balloon has a working length diameter of about 7 mm,
 6.2 to 11.4 mm when the balloon has a working length diameter of about 8 mm,
 6.7 to 13.3 mm when the balloon has a working length diameter of about 9 mm,
 8.1 to 15.2 mm when the balloon has a working length diameter of about 10 mm,
 9.1 to 17.1 mm when the balloon has a working length diameter of about 11 mm,
 9.9 to 19.1 mm when the balloon has a working length diameter of about 12 mm,
 11.2 to 22.9 mm when the balloon has a working length diameter of about 14 mm, or
 13.3 to 25.4 mm when the balloon has a working length diameter of about 15 mm;
 (b) inflating the balloon by providing a fluid to a catheter lumen in fluid communication with the balloon;
 (c) deflating the balloon; and
 (d) applying a force to the dilation catheter, so the balloon is withdrawn through the conduit.

10. The method of claim 9, where the radius is from:
 1.3 to 3.3 mm when the balloon has a working length diameter of about 3 mm,
 2.5 to 4.7 mm when the balloon has a working length diameter of about 4 mm,
 3.2 to 6.4 mm when the balloon has a working length diameter of about 5 mm,
 4.7 to 8.3 mm when the balloon has a working length diameter of about 6 mm,
 6.4 to 10.2 mm when the balloon has a working length diameter of about 7 mm,
 8.3 to 11.4 mm when the balloon has a working length diameter of about 8 mm,
 8.9 to 13.3 mm when the balloon has a working length diameter of about 9 mm,
 10.8 to 15.2 mm when the balloon has a working length diameter of about 10 mm,
 12.1 to 17.1 mm when the balloon has a working length diameter of about 11 mm,
 13.3 to 19.1 mm when the balloon has a working length diameter of about 12 mm,
 14.9 to 22.9 mm when the balloon has a working length diameter of about 14 mm, or
 17.8 to 25.4 mm when the balloon has a working length diameter of about 15 mm.

11. The method of claim 9, where the radius is:
 about 2.5 mm when the balloon has a working length diameter of about 3 mm,
 about 3.2 mm when the balloon has a working length diameter of about 4 mm,
 about 4.7 mm when the balloon has a working length diameter of about 5 mm,
 about 6.4 mm when the balloon has a working length diameter of about 6 mm,
 about 8.3 mm when the balloon has a working length diameter of about 7 mm,
 about 8.9 mm when the balloon has a working length diameter of about 8 mm,
 about 10.8 mm when the balloon has a working length diameter of about 9 mm,
 about 12.1 mm when the balloon has a working length diameter of about 10 mm,
 about 13.3 mm when the balloon has a working length diameter of about 11 mm,
 about 14.9 mm when the balloon has a working length diameter of about 12 mm,
 about 17.8 mm when the balloon has a working length diameter of about 14 mm, or
 about 19.1 mm when the balloon has a working length diameter of about 15 mm.

* * * * *

UNITED STATES PATENT AND TRADEMARK OFFICE
CERTIFICATE OF CORRECTION

PATENT NO. : 8,382,787 B2
APPLICATION NO. : 10/593376
DATED : February 26, 2013
INVENTOR(S) : David G. Burton et al.

Page 1 of 1

It is certified that error appears in the above-identified patent and that said Letters Patent is hereby corrected as shown below:

In the Claims

In column 8, claim 1, line 17, after "diameter of about" replace "0.3 mm," with --3 mm,--.

Signed and Sealed this
Thirtieth Day of July, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,382,787 B2 | Page 1 of 1 |
| APPLICATION NO. | : 10/593376 | |
| DATED | : February 26, 2013 | |
| INVENTOR(S) | : Burton et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1472 days.

Signed and Sealed this
Fourth Day of November, 2014

Michelle K. Lee
*Deputy Director of the United States Patent and Trademark Office*